(12) United States Patent
Kolb et al.

(10) Patent No.: US 6,891,068 B2
(45) Date of Patent: May 10, 2005

(54) WATER AS PROMOTER IN THE NUCLEOPHILIC SUBSTITUTION OF CHLORIDE

(75) Inventors: Hartmuth C. Kolb, San Diego, CA (US); Zhi-Cai Shi, South Brunswick, NJ (US); Zhi-Min Wang, North Brunswick, NJ (US)

(73) Assignee: Lexicon Pharmaceuticals, Inc., New Brunswick, NJ (US)

( * ) Notice: Subject to any disclaimer, the term of this patent is extended or adjusted under 35 U.S.C. 154(b) by 0 days.

(21) Appl. No.: 10/391,865

(22) Filed: Mar. 19, 2003

(65) Prior Publication Data

US 2004/0015018 A1 Jan. 22, 2004

Related U.S. Application Data

(60) Provisional application No. 60/365,567, filed on Mar. 19, 2002.

(51) Int. Cl.$^7$ ............................................... C07C 209/08

(52) U.S. Cl. .................. 564/445; 548/331.1; 548/331.5
(58) Field of Search ....................... 564/445; 548/331.1, 548/331.5

(56) References Cited

PUBLICATIONS

Database CASREACT on STN, No. 103:37072, Carretero et al., J. Chem Research, Synopses (1985), vol. 1, p. 6–7 (abstract).*

Carretero et al., J. Chem Research, Synopses (1985), vol. 1, p. 6–7.*

Effenberger et al., Chem. Ber. (1998), 121(12), p. 2209–23.*

* cited by examiner

*Primary Examiner*—Brian Davis
(74) *Attorney, Agent, or Firm*—McDonnell Boehnen Hulbert & Berghoff

(57) ABSTRACT

Disclosed is a one step method for preparing a β-substituted sulfide by treating a β-halosulfide with a nucleophile in water.

10 Claims, No Drawings

WATER AS PROMOTER IN THE NUCLEOPHILIC SUBSTITUTION OF CHLORIDE

BACKGROUND OF THE INVENTION

1. Field of the Invention

This invention relates to the use of a protic solvent in nucleophilic displacement reactions.

2. Description of the Related Art

Nucleophilic substitution of alkyl halides is perhaps one of the most useful reactions in organic chemistry. The nucleophilic displacement of chloride ion and similar leaving groups (e.g. bromide ion, sulfonate ion) is usually performed under anhydrous conditions using polar aprotic solvents or alcoholic solvents, or heterogeneous phase transfer conditions. This is especially true for very reactive substrates, since protic solvents (or water) might lead to solvolysis of these substrates.

One such example of very reactive intermediates is the sulfonium ion that forms in nucleophilic displacement reactions of β-chlorosulfides. As fast as it is formed, this intermediate reacts with water to yield the corresponding solvolysis product. Thus, known procedures for the nucleophilic displacement of such compounds typically employ aprotic solvents (THF, DMF, DMSO, MeCN), or alcoholic solvents (EtOH), phase transfer conditions or no solvent (Ohsawa et al., *J. Org. Chem.* 1983 48, 3644; Tolstikov et al., *Khim-Farm. Zh.* 1997 31 (8), 26–29; Krivonogov et al., *Khim-Farm. Zh.* 1995 29 (4), 38–40). Usually these procedures require harsh conditions (e.g. temperatures over 100° C.) and, as such, products are isolated in poor to moderate yields. A procedure that reduces reaction time and increases reaction yield is desired.

SUMMARY OF THE INVENTION

This invention provides for a process of using water as solvent/promotor in the nucleophilic displacement of halogens. Specifically, water is used as a co-solvent in nucleophilic halide displacement reactions of β-halosulfides. It is believed that water facilitates the formation of the intermediate sulfonium ion, which subsequently reacts with the desired nucleophile to form the desired product.

DETAILED DESCRIPTION OF THE INVENTION

According to Scheme 1, a preferred embodiment of the present invention relates to a method for the formation of a β-substituted sulfide III by reacting a β-halosulfide I with a desired nucleophile II in water, and optionally, another solvent or other solvents.

Scheme 1

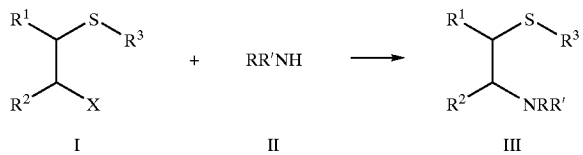

In Scheme 1:
R, R', $R^1$, and $R^2$ independently are hydrogen or
R, R', $R^1$, $R^2$ and $R^3$ independently are
 lower alkyl optionally substituted with one, two or three groups independently selected from halogen, lower alkoxy, —C(O)-alkyl, aryl, —C(O)NH-alkyl, C(O)N-dialkyl, —C(O)O-alkyl, —$SO_2NR^4R^5$, cyano, alkenyl or alkynyl, or aryl, arylalkyl, heteroaryl or heteroarylalkyl wherein the ring portion of each is optionally substituted with one, two or three groups independently selected from halogen, lower alkyl, lower alkoxy, —C(O)-alkyl, —C(O)NH-alkyl, C(O)N-dialkyl, —C(O)O-alkyl, —$SO_2NR^4R^5$, cyano, alkenyl or alkynyl; or $R^1$ and $R^2$ together with the carbon atom to which they are attach form a 3, 4, 5, 6, or 7 membered carbocyclic ring up to two of which members are optionally hetero atoms selected from oxygen, sulfur and nitrogen, where the carbocyclic group is optionally substituted with one or two groups halogen, lower alkoxy, —C(O)-alkyl, hydroxy, —C(O)NH-alkyl, C(O)N-dialkyl, —C(O)O-alkyl, —$SO_2NR^4R^5$, cyano, alkenyl or alkynyl; and $R^4$ and $R^5$ independently are hydrogen or lower alkyl.

By "alkyl", "lower alkyl", and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. These groups may be substituted with up to four groups mentioned below for substituted aryl.

By "alkoxy", "lower alkoxy", and "$C_1$–$C_6$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. These groups may be substituted with up to four groups mentioned below for substituted aryl.

By the term "halogen" in the present invention is meant fluorine, bromine, chlorine, and iodine.

A "carbocyclic group" or "cycloalkyl" is a nonaromatic cyclic ring or fused rings having from 3 to 7 ring members. Examples include cyclopropyl, cyclobutyl, and cycloheptyl. These rings may be substituted with one or more of the substituent groups mentioned below for aryl, for example alkyl, halo, and alkoxy. Typical substituted carbocyclic groups include 2-chlorocyclopropyl, 2,3-diethoxycyclopentyl, and 2,2,4,4-tetrafluorocyclohexyl. The carbocyclic group may contain one or two heteroatoms selected from oxygen, sulfur, and nitrogen, and such ring systems may be referred to as "heterocyclyl" or "heterocyclic". Examples include pyranyl, tetrahydrofuranyl, and dioxanyl. These heterocyclyl groups may be substituted with up to four of the substituent groups mentioned for aryl to give groups such as 3-chloro-2-dioxanyl, and 3,5-dihydroxymorpholino. In addition, the carbocyclic or heterocyclic group may also contain one or more internal double bonds, as long as having such double bonds does not make the carbocycle or hererocycle aromatic.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. The heteroaryl group is optionally substituted with up to four groups mentioned below for substituted aryl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, trifluoromethyl, trifluoromethoxy, lower acyloxy, aryl, heteroaryl, and nitro.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In a preferred embodiment, the β-halosulfide I and the desired nucleophile II are reacted together in water and an additional suitable co-solvent. The reaction mixture in such a solvent can be homogenous or heterogenous. Examples of suitable solvents for the present method include, but are not limited to, one or more of the following: a protic solvent such as methanol, ethanol, n-propanol, or n-butanol; or aprotic solvents such as tetrahydrofuran (THF), acetonitrile, dimethylsulfoxide, dimethylformamide or hexamethylphosphorotriamide. In an even more preferred embodiment, the solvent is an aprotic solvent, and most preferably, THF.

In another preferred embodiment, the method of the present invention is carried out at temperatures of from between 20° C. and 200° C. More preferably, the reaction temperature is from between 60° C. and 150° C. and even more preferably the reaction temperature is from between 75° C. and 100° C.

In yet another preferred embodiment, a suitable base is present in the reaction mixture. Examples of acceptable bases used in the present method are those with alkali metals or alkaline earth metals such as sodium, potassium, calcium and magnesium, and those with organic bases including, but not limited to, amines. Preferred bases are organic bases, such as, for example, triethyl amine. In an even more preferred embodiment, the base is present in a molar excess amount.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

EXAMPLE 1

Synthesis of Iso-butyl(2-phenylthiocyclopentyl) amine

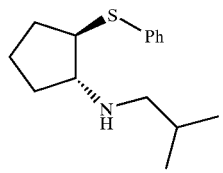

1-Chloro-2-phenylthiocyclopentane (10 g, 47 mmol) and iso-butyl amine (4.13 g, 56.4 mmol) are dissolved in 50 ml of THF. Triethylamine (13.1 ml) and water (10 ml) are added to the reaction and the resulting mixture is refluxed at 80° C. overnight. The reaction mixture is cooled down to room temperature and 200 ml of dichloromethane is added to dilute the reaction mixture. The reaction mixture is then dried over $K_2CO_3$ ($K_2CO_3$ also neutralizes the triethylamine/HCl salt, which is generated during the reaction). Removal of the solvent gives crude product as a viscous oil, which is purified by distillation to give pure product 7.1 g (Compound 1) (yield: 53%).

EXAMPLE 2

The following compounds are prepared essentially according to the procedures described in Example 1 (10 g scale) and shown in Scheme 1:

(a) Benzyl(2-phenylthiocyclopentyl)amine (58% yield) (Compound 2);

(b) n-Propyl(2-phenylthiocyclopentyl)amine (45% yield) (Compound 3);

(c) (2-Methoxyethyl)-(2-phenylthiocyclopentyl)amine (62% yield) (Compound 4);

(d) Methyl(2-phenylthiocyclopentyl)amine (65% yield) (Compound 5);

(e) (3-Imidazol-1-ylpropyl)-(2-phenylthiocyclopentyl) amine (55% yield) (Compound 6).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of preparing a β-substituted sulfide of the formula

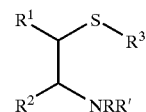

comprising reacting a β-halosulfide of the formula

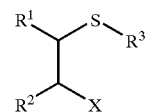

with a nucleophile of the formula RR'NH in water, wherein

X is halogen;

R, R', $R^1$, and $R^2$ independently are hydrogen or

R, R', $R^1$, $R^2$ and $R^3$ independently are lower alkyl optionally substituted with one, two or three groups independently selected from halogen, lower alkoxy, —C(O)-alkyl, aryl, —C(O)NH-alkyl, C(O)N-dialkyl, —C(O)O-alkyl, —SO$_2$NR$^4$R$^5$, cyano, alkenyl or alkynyl, or aryl, arylalkyl, heteroaryl or heteroarylalkyl wherein the ring portion of each is optionally substituted with one, two or three groups independently selected from halogen, lower alkyl, lower alkoxy, —C(O)-alkyl, —C(O)NH-alkyl, C(O)N-dialkyl, —C(O)O-alkyl, —$SO_2NR^4R^5$, cyano, alkenyl or alkynyl; or $R^1$ and $R^2$ together with the carbon atom to which they are attached form a 3, 4, 5, 6, or 7 membered carbocyclic ring up to two of which members are optionally hetero atoms selected from oxygen, sulfur and nitrogen, where the carbocyclic group is optionally substituted with one or two groups independently selected from halogen, lower alkoxy, —C(O)-alkyl, —C(O)NH-alkyl, C(O)N-dialkyl, —C(O)O-alkyl, —$SO_2NR^4R^5$, cyano, alkenyl or alkynyl; and $R^4$ and $R^5$ independently are hydrogen or lower alkyl.

2. A method according to claim 1 wherein a co-solvent is present.

3. A method according to claim 2 wherein the co-solvent is an aprotic solvent.

4. A method according to claim 3 wherein the co-solvent is THF.

5. A method according to claim 1 further comprising reacting the β-halosulfide with the nucleophile in water at a temperature of from between 20 to 200° C.

6. A method according to claim 5 wherein the temperature is from between 75 to 100° C.

7. A method according to claim 1 further comprising reacting the β-halosulfide with the nucleophile in water in the presence of a base.

8. A method according to claim 7 wherein the base is an organic base.

9. A method according to claim 8 wherein the base is an amine.

10. A method according to claim 7 wherein the base is present in a molar excess amount.

* * * * *